United States Patent [19]

Hinohara et al.

[11] Patent Number: 5,465,733
[45] Date of Patent: Nov. 14, 1995

[54] GUIDE WIRE FOR CATHETERS AND METHOD FOR ITS USE

[76] Inventors: Tomoaki Hinohara, 40 Los Charos La., Portola Valley, Calif. 94028; James W. Vetter, 1812 Sand Hill Rd. #201, Palo Alto, Calif. 94303

[21] Appl. No.: 137,321

[22] Filed: Oct. 14, 1993

[51] Int. Cl.⁶ ............................................. A61M 25/00
[52] U.S. Cl. ........................................... 128/772; 128/657
[58] Field of Search ............................... 128/772, 657; 604/95, 103, 104, 170, 280, 282

[56] References Cited

U.S. PATENT DOCUMENTS

| | | | |
|---|---|---|---|
| 3,913,565 | 10/1975 | Kawahara | 128/772 |
| 4,195,637 | 4/1980 | Grüntzig et al. | 128/348 |
| 4,323,071 | 4/1982 | Simpson et al. | 128/343 |
| 4,490,421 | 12/1984 | Levy | 428/35 |
| 4,538,622 | 9/1985 | Samson et al. | 128/772 |
| 4,545,390 | 10/1985 | Leary | 128/772 |
| 4,616,653 | 10/1986 | Samson et al. | 128/657 X |
| 4,619,274 | 10/1986 | Morrison | 128/772 |
| 4,643,194 | 2/1987 | Fogarty | 128/772 X |
| 4,654,024 | 3/1987 | Crittenden et al. | 604/49 |
| 4,724,846 | 2/1988 | Evans, III | 128/772 |
| 4,748,982 | 6/1988 | Horzewski et al. | 128/344 |
| 4,762,129 | 8/1988 | Bonzel | 128/344 |
| 4,775,371 | 10/1988 | Mueller, Jr. | 604/280 |
| 4,787,399 | 11/1988 | Bonello et al. | 128/772 |
| 4,827,941 | 5/1989 | Taylor et al. | 128/657 |
| 4,832,047 | 5/1989 | Sepetka et al. | 128/657 X |
| 4,875,489 | 10/1989 | Messner et al. | 128/772 |
| 4,884,579 | 12/1989 | Engleson | 128/772 |
| 4,917,103 | 4/1990 | Gambale et al. | 128/772 |
| 4,922,923 | 5/1990 | Gambale et al. | 128/772 |
| 4,955,862 | 9/1990 | Sepetka | 604/282 X |
| 4,988,356 | 1/1991 | Crittenden et al. | 606/192 |
| 5,031,636 | 7/1991 | Gambale et al. | 128/772 |
| 5,040,548 | 8/1991 | Yock | 128/898 |
| 5,047,045 | 9/1991 | Arney et al. | 606/194 |
| 5,055,024 | 10/1991 | Jackowski et al. | 425/140 |
| 5,060,660 | 10/1991 | Gambale et al. | 128/772 |
| 5,061,273 | 10/1991 | Yock | 606/194 |
| 5,133,364 | 7/1992 | Palermo et al. | 128/772 |
| 5,141,494 | 8/1992 | Danforth et al. | 604/96 |
| 5,167,239 | 12/1992 | Cohen et al. | 128/657 X |
| 5,243,996 | 9/1993 | Hall | 128/657 X |
| 5,303,714 | 4/1994 | Abele et al. | |

FOREIGN PATENT DOCUMENTS

9213589  8/1992  WIPO .......................... A61M 29/00

*Primary Examiner*—Sam Rimell
*Attorney, Agent, or Firm*—James J. Leary; Carol A. Duffield

[57] ABSTRACT

An improved guide wire for use with cardiovascular catheters, particularly angioplasty or balloon dilatation catheters. The guide wire has a solid core wire which makes up the proximal end of the guide wire. The core wire is tapered toward the distal end to increase flexibility. The tapered distal end of the core wire is surrounded by a coil spring, which may be made completely or partially from a highly radiopaque material. A tapered transition device is attached to the coil spring at a selected distance from the distal end of the guide wire. The transition device is roughly bullet-shaped with a tapered distal edge which provides a smooth transition to aid the dilatation catheter in crossing a stenosis. The tapered transition device also serves to predilate very tight stenoses, making it easier to cross the lesion with an angioplasty balloon or other therapeutic device. The transition device can be made of metal or plastic with a radiopaque filler for easier visualization by x-ray or fluoroscopy. A removably attachable handle for maneuvering the guide wire and a method of use for the improved guide wire are also disclosed. An angioplasty catheter with a reinforced proximal shaft, which allows easier one-handed operation of the catheter and guide wire system, is also presented.

20 Claims, 7 Drawing Sheets

GUIDE WIRE FOR CATHETERS AND METHOD FOR ITS USE

FIELD OF INVENTION

The present invention relates to an improved guide wire for use with cardiovascular catheters. More particularly it relates to a guide wire with a tapered transition device to aid in advancing a catheter, such as a balloon angioplasty catheter, through a tight stenosis or other narrowing in a patient's vasculature.

BACKGROUND OF THE INVENTION

The guide wire of the present invention finds particular use in performing balloon dilatation or other medical procedures where a catheter must be advanced through a narrowing in an artery, a vein or other body passage. Balloon dilatation, alternately known as percutaneous transluminal angioplasty (PTA) or percutaneous transluminal coronary angioplasty (PTCA), is a procedure in which a catheter having a cylindrical balloon mounted at its distal end is inserted into a stenosis or a narrowing in an artery. The balloon is inflated with a pressurized fluid to dilate the stenosis. Once the stenosis has been dilated and normal blood flow has been reestablished, the balloon is deflated and the catheter is withdrawn. A procedure for performing PTCA is described in U.S. Pat. No. 4,195,637, granted to Andreas Grüntzig and Hans Gleichner, the specification of which is hereby incorporated by reference in its entirety. The dilatation catheter described by Grüntzig and Gleichner is known as fixed-tip catheter because it has a short guide wire permanently attached to the distal end of the catheter.

Dr. Grüntzig achieved an 80% clinical success rate in the first 1500 PTCA cases with his fixed-tip dilatation catheter system. In approximately 20% of the cases, however, he did not succeed in dilating the stenosis. The clinical difficulties cited by Dr. Grüntzig included:

1) failure to reach the stenotic lesion with the dilatation catheter,
2) failure to cross the stenosis with the dilatation balloon,
3) failure to dilate the lesion.

Failure to reach the stenosis was typically caused by tortuosity in the coronary arteries or branching of the coronary arteries proximal to the lesion, which could not be negotiated by the catheter. Failure to cross the stenosis with the dilatation catheter could be caused by the deflated balloon catheter being too large in diameter to pass a tight stenosis or too much friction between the balloon catheter and the arterial walls entering the lesion. Failure to dilate the stenosis was caused by the lesion being too resistant to being dilated and the inability of the balloon catheter to achieve high dilating pressures. High resistance to dilation can be caused by a lesion which is calcified or highly fibrotic or by a muscular spasm of the arterial walls. These clinical difficulties spurred Grüntzig and others to improve upon the basic technique of balloon angioplasty.

An improved procedure for performing PTCA is described in U.S. Pat. No. 4,323,071 granted to John B. Simpson and Edward W. Robert, the specification of which is also incorporated herein by reference in its entirety. In this improved technique, the dilatation catheter is made with a guide wire lumen through the entire length of the catheter. The catheter is introduced over a small diameter guide wire which helps to maneuver the catheter through the coronary arteries. A further advance in this over-the-wire technique was the introduction of a steerable guide wire for balloon dilatation procedures, which is described in U.S. Pat. No. 4,545,390 granted to James J. Leary. Further refinements of the steerable guide wire are described in U.S. Pat. No. 4,538,622 granted to Wilfred J. Samson and Ronald G. Williams. The specifications of U.S. Pat. Nos. 4,545,390 and 4,538,622 are hereby incorporated by reference in their entirety. The steerable guide wire allows a balloon catheter to be negotiated through tortuous or branching coronary arteries in order to dilate difficult to reach stenoses. These advances greatly improved the clinical success of the balloon dilatation procedure and allowed the technique to be applied to coronary lesions which were previously unreachable.

The problem of being unable to cross a lesion once it had been reached was also being addressed by various advances in dilatation catheters. The adoption of the over-the-wire technique increased the ability to cross tight lesions because the guide wire could be advanced across the stenosis ahead of the catheter to provide a path for the catheter to follow. Competitors, meanwhile, introduced smaller diameter fixed-tip catheters which had a smoother transition from the guide wire tip to the balloon to make it easier to cross tight stenotic lesions. Other advances which improved the "crossability" of dilatation catheters included the use of more lubricious materials for the catheter and balloon and, later, the addition of lubricious coatings to the outside of the catheter and the guide wire so that they could slip past the lesion with less difficulty.

Another area of advancement in dilatation catheters has been in the improvement of the balloon material itself. These improvements addressed both the ability to cross tight lesions with the balloon and the ability for the balloon to dilate highly resistant stenoses. The progression in balloon materials was from polyvinylchloride to radiation crosslinked polyethylene, then to truly high strength materials such as oriented polyamide or polyethylene terephthalate. One process for producing polyamide balloons is described in U.S. Pat. No. 5,055,024, another for polyethylene terephthalate balloons is described in U.S. Pat. No. 4,490,421. By using high strength materials, greater pressure capacity could be achieved with a lesser wall thickness in the balloons, giving the catheter a lower deflated profile which makes it easier to cross tight stenoses.

Despite these tremendous improvements in dilatation catheters, the choice of whether to use a fixed-tip catheter or an over-the-wire system for balloon angioplasty still involves a compromise in performance. The over-the-wire system allows greater maneuverability of the guide wire and the catheter by the physician and, with newly introduced techniques, it also allows exchange of the balloon catheter while leaving the guide wire in place across the lesion. The advanced fixed-tip catheters, on the other hand, provide a lower deflated profile and a smoother transition from the guide wire tip to the balloon so that even very tightly stenotic lesions can be crossed. One attempt to bridge the compromise between these two approaches is a catheter with a "captive" guide wire described in U.S. Pat. No. 4,616,653, granted to Wilfred J. Samson and Jeffrey S. Frisbie. This catheter provides a lower deflated profile and a fairly smooth balloon transition, while allowing semi-independent maneuvering of the guide wire. However, neither the fixed-tip catheters nor this captive guide wire catheter allow catheter exchanges while the guide wire is left in place.

Catheter exchange has become clinically important in recent years, bolstered by the introduction of extendible guide wires and, more recently, "monorail" or rapid exchange catheters. It is important that new guide wire introductions be capable of being used in conjunction with both of these catheter exchange systems. Examples of extendible guide wires can be found in U.S. Pat. No. 5,133,364, granted to Thomas J. Palermo and Stephen M. Salmon, and U.S. Pat. No. 5,060,660, granted to Richard A. Gambale, and U.S. Pat. Nos. 5,031,636, 4,922,923, and 4,917,103, granted to Richard A. Gambale, James F. Crittenden, and James P. Ryan, U.S. Pat. No. 4,875,489 granted to Kirsten L. Messner, Robert M. Abrahms, and Ray R. Beitelia, and U.S. Pat. No. 4,827,941 granted to Taylor et al., the specifications of which are hereby incorporated by reference in their entirety. Examples of rapid exchange catheters can be found in U.S. Pat. No. 4,762,129, granted to Tassilo Bonzel, U.S. Pat. No. 4,988,356, granted to James F. Crittenden, U.S. Pat. No. 4,748,982 granted to Michael J. Horzewski and Paul G. Yock, and U.S. Pat. Nos. 5,040,548 and 5,061,273 granted to Paul G. Yock, the specifications of which are also hereby incorporated by reference in their entirety. Rapid exchange catheters such as those described in these patents often have the drawback that they lack the same level of "pushability" as true over-the-wire catheters which makes them more difficult to push across tightly stenotic lesions.

Another related drawback of the current over-the-wire balloon dilatation catheter systems is that the transition between the guide wire and the distal tip of the catheter presents a step, which not only makes it difficult to cross the lesion as previously mentioned, but also can scrape or gouge the atherosclerotic material in the lesion or the arterial wall. One consequence of this can be dissection of the arterial wall. Another possible consequence can be embolization of particles of the atherosclerotic material from the lesion or scraping the endothelium from the artery wall as the catheter passes. Irritating the artery wall by scraping can cause a muscular spasm of the artery walls which can interfere with the catheterization or cause a reduction in blood flow which exacerbates the patient's condition. It has also been theorized that removing the endothelium from the artery walls creates a new site for growth of atherosclerotic plaque or medial hyperplasia which can further compromise blood flow through the arteries. The present invention provides an improved guide wire and a technique for its use which seek to eliminate the compromises in performance involved in using an over-the-wire balloon dilatation system.

SUMMARY OF THE INVENTION

In keeping with the foregoing discussion, the objective of the present invention is to provide an improved guide wire for use with catheters, particularly for use with an over-the-wire balloon dilatation catheter. The guide wire must be independently maneuverable from the catheter to assist in placing the catheter at a desired position in a patient's vasculature. Another objective is to provide a guide wire with a tapered transition device which creates a smooth transition between the guide wire and the catheter tip or balloon. The smooth transition created by the tapered transition device has the dual objective of 1) assisting the catheter to cross tightly stenotic lesions more easily and 2) to eliminate any step between the guide wire and the catheter tip which could scrape the arterial walls.

A further objective of the improved guide wire is that it should allow catheter exchanges while the guide wire is left in place. This includes the ability to make catheter exchanges using a guide wire extension, as well as the ability to use the guide wire with "monorail" or rapid exchange catheter systems. Another objective is that the guide wire should provide extra "pushability" for the catheter. Increased pushability also helps to maneuver the catheter across tightly stenotic lesions. Some rapid exchange catheters have been criticized for not having enough pushability, which makes this attribute especially important for use with rapid exchange catheters.

Another important objective of the invention is to make the catheter and guide wire system easier to operate. The goal is to allow one-handed operation of the catheter and guide wire. One aspect of this objective is to provide a removably attachable handle for maneuvering the guide wire which is especially adapted for using the guide wire with an over-the-wire balloon dilatation catheter. Another aspect is to provide improvements for the catheter which allow easier one-handed operation when used in cooperation with the guide wire.

In accordance with these objectives, the present invention takes the form of a small diameter guide wire which has a solid core wire which makes up the proximal end of the guide wire. The core wire is tapered toward the distal end to increase flexibility. The tapered distal end of the core wire is surrounded by a coil spring, which may be made completely or partially from a highly radiopaque material. A tapered transition device is attached to the coil spring at a selected distance from the distal end of the guide wire. The transition device is roughly bullet-shaped with many possible variations of the shape. The transition device can be made of metal or plastic. If a plastic material is used for the transition device it should be made with a radiopaque filler for easier visualization by x-ray or fluoroscopy. A removably attachable handle for maneuvering the guide wire and a method of use for the improved guide wire are also disclosed. An angioplasty catheter with a reinforced proximal shaft, which allows easier one-handed operation of the catheter and guide wire system, is also presented. Other objects and advantages of the invention will no doubt occur to those skilled in the art upon reading and understanding the following detailed description along with the accompanying drawings.

DETAILED DESCRIPTION OF THE INVENTION

Figure 1:
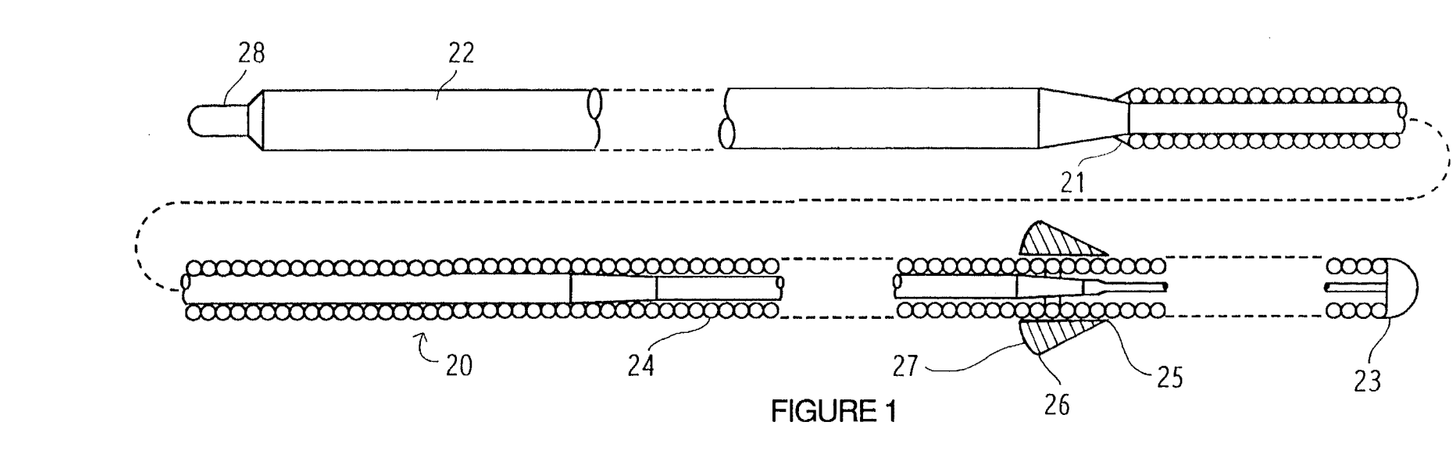
FIG. 1 shows a cross section of the guide wire with tapered transition device.

FIG. 1 shows a first preferred embodiment of the guide wire with tapered transition device. The guide wire 20 is constructed with a tapered metal core wire 22 which extends substantially the whole length of the guide wire 20. The core wire 22 is preferably made of stainless steel, such as 304V stainless steel. Other acceptable metal alloys for the core wire 22 include high strength cobalt alloys, such as Elgiloy or Carpenter MP35N, and superelastic nickel-titanium alloys, such as Nitinol or Tinel. The core wire 22 is tapered on its distal end by conventional means, such as by centerless grinding. For ease of centerless grinding and for proper performance of the finished guide wire 20, the core wire 22 should be straightened using a rotary wire straightener and stress relief annealed prior to the taper grinding. The distal end of the core wire 22 can be tapered in stages, as shown, or it can be made with a continuous conical taper. The taper on the core wire 22 increases the flexibility of the distal end of the guide wire 20. If an extremely flexible distal end is desired on the guide wire 20, the distal end of the core wire can be flattened to reduce its bending stiffness without reducing its tensile strength. Alternatively, a flat wire of stainless steel, or a more flexible alloy such as platinum/7% tungsten, can be joined to the distal end of the core wire by welding, soldering or brazing to create a very flexible distal section. The proximal end of the core wire 22 can be made with a short tapered section 28 to create a connector for attachment of a guide wire extension, as described in the prior art.

The tapered distal end of the core wire 22 is surrounded by a fine coil spring 24, which is preferably made of a springy and highly radiopaque metal alloy, such as platinum/ 7% tungsten. Alternatively, the coil spring 24 can be made of stainless steel if high radiopacity is not required or a stainless steel coil spring can be joined end-to-end with a highly radiopaque coil spring of platinum/7% tungsten, as described in the prior art to reduce the amount of precious metal needed. The coil spring 24 is joined to the core wire 22 at its proximal and distal extremities. The proximal joint 21 should form a smooth transition between the core wire 22 and the proximal edge of the coil spring 24, without sudden steps or sharp edges. The distal joint 23 should be made so that it forms a smooth, hemispherical tip on the end of the guide wire. The joints can be made by welding, brazing or soldering. Welding techniques which have been found to be effective for the distal joint include TIG welding and plasma arc welding. Brazing techniques effective for the proximal and distal joints include brazing with gold or silver based brazing fillers. A brazing filler with a melting point below 1200° F. is preferred to avoid annealing or other thermal damage to the guide wire components. The brazing filler can be powdered and made into a brazing paste by mixing it with a flux appropriate for the guide wire materials. Soldering is preferably done with tin/silver solder because of its high strength and low toxicity compared to conventional solders.

A tapered transition device 26 is attached to the guide wire intermediate the proximal and distal ends of the coil spring. The tapered transition device 26 can be made of stainless steel, or a more radiopaque alloy such as a gold or platinum based alloy. Alternatively, the tapered transition device 26 can be made of a polymer or a polymer alloy with a radiopaque filler. The tapered transition device 26 can be brazed, soldered or glued to the coil spring 24 of the guide wire 20, as appropriate for the materials used. The coil spring 24 should also be joined to the core wire at the point where the tapered transition device 26 is attached to provide better transmission of push and torque from the core wire The distal edge 25 of the tapered transition device 26 is made with a smooth taper, shown as an acute conical taper in this illustrative embodiment. The outer diameter of the tapered transition device 26 should closely match the diameter of the distal tip of the catheter that the guide wire will be used with. The proximal edge 27 of the tapered transition device 26 should be rounded off as shown to avoid any exposed sharp edges. The entire guide wire assembly 20 is preferably coated with a lubricious coating, such as Teflon or silicone or a lubricious hydrophylic coating.

The following are given as typical measurements for the guide wire with tapered transition device. These dimensions are intended to illustrate only some of the many possible embodiments of the invention and should not be taken as limiting. When intended for use with coronary dilatation catheters, the total length of the guide wire 20 is typically in the range of 175 cm. In use, the guide wire length can be extended by the addition of a guide wire extension to the connector 28 on the proximal end of the core wire 22. The coil spring 24 which surrounds the tapered distal end of the core wire 22 is typically 15 to 30 cm in length, leaving the remainder of the core wire 22 on the proximal end unground. For applications other than PTCA, the desired length of the guide wire 20 and the coil spring 24 may be different. The diameter of the coil spring 24 and the unground portion of the core wire 22 is typically 0.014, 0.016 or 0.018 inches, although for some applications the diameter could be as small as 0.008 inches or as large as 0.038 inches or larger. As mentioned above, the diameter of the tapered transition device 26 should closely match the diameter of the distal tip of the catheter that the guide wire will be used with. In a typical embodiment for use with a standard PTCA catheter, the tapered transition device 26 has a diameter of about 0.030 inches and a length of about 0.040 inches. The tapered transition device 26 is typically attached to the coil spring 24 of the guide wire 20 between 2 and 5 cm from the distal tip of the guide wire. A special "push" version of the guide wire can be made by extending the relatively stiffer proximal tapered section of the core wire up to the point where the tapered transition device is attached to the guide wire, and having the flexible distal section of the guide wire extend from the tapered transition device 26 to the distal tip. The dimensions given can vary greatly depending on the design of the catheter and the medical procedure that it is intended to be used for.

Figure 2:
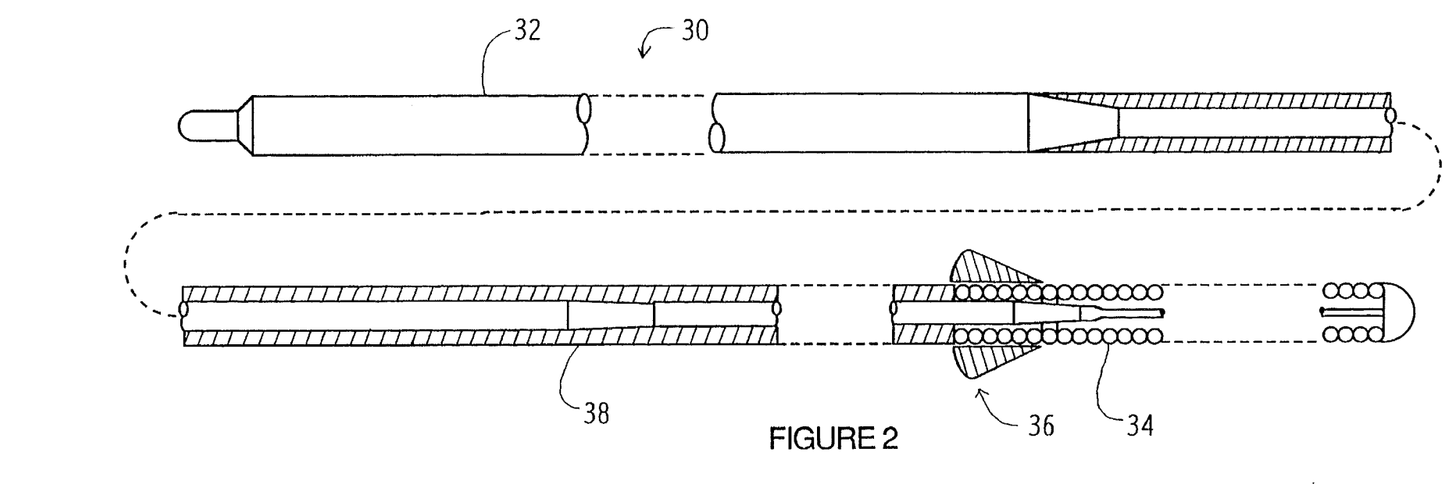
FIG. 2 shows a cross section of an alternate embodiment of the guide wire with tapered transition device.

FIG. 2 shows an alternate embodiment of the guide wire with tapered transition device. Similar to the first embodiment, the guide wire 30 is constructed with a tapered metal core wire 32 which extends substantially the whole length of the guide wire 30. The tapered distal end of the core wire 32 is surrounded by a fine coil spring 34, which extends from the tapered transition device 36 to the distal tip of the guide wire. The part of the tapered distal end of the core wire 32 proximal to the tapered transition device 36 is surrounded by a flexible and lubricious polymeric tube 38, such as Teflon or polyethylene. Alternatively, the polymeric tube 38 can be made of polyurethane or another suitable polymer with a lubricious hydrophylic coating. If desired, the polymeric tube 38 can be made with a radiopaque filler material to improve the radiopacity of the guide wire. The polymeric tube 38 can be assembled to the core wire 32 by extruding a tube of the appropriate dimensions and placing it coaxially over the core wire 32 before attachment of the tapered transition device 36 and the coil spring 34. The polymeric tube 38 can be glued to the core wire 32 or heat sealed to the core wire 32 by drawing the assembly through a heated die. Alternatively, the polymeric tube 38 can be applied by shrinking a polymeric heat-shrink tubing onto the core wire 32, with or without an additional adhesive. The polymeric tube 38 could also be formed by applying a polymeric coating to the core wire 32 by overextrusion or other coating techniques.

This embodiment has the advantage that it reduces the amount of precious metal needed for the coil spring 34. It also potentially improves the performance of the guide wire because the polymeric tube 38 can be made with a smoother and more lubricious surface than the coil spring 34. The polymeric tube 38 also provides a better substrate for coating with a lubricious hydrophylic coating than the metal spring coil 34.

Figure 3:
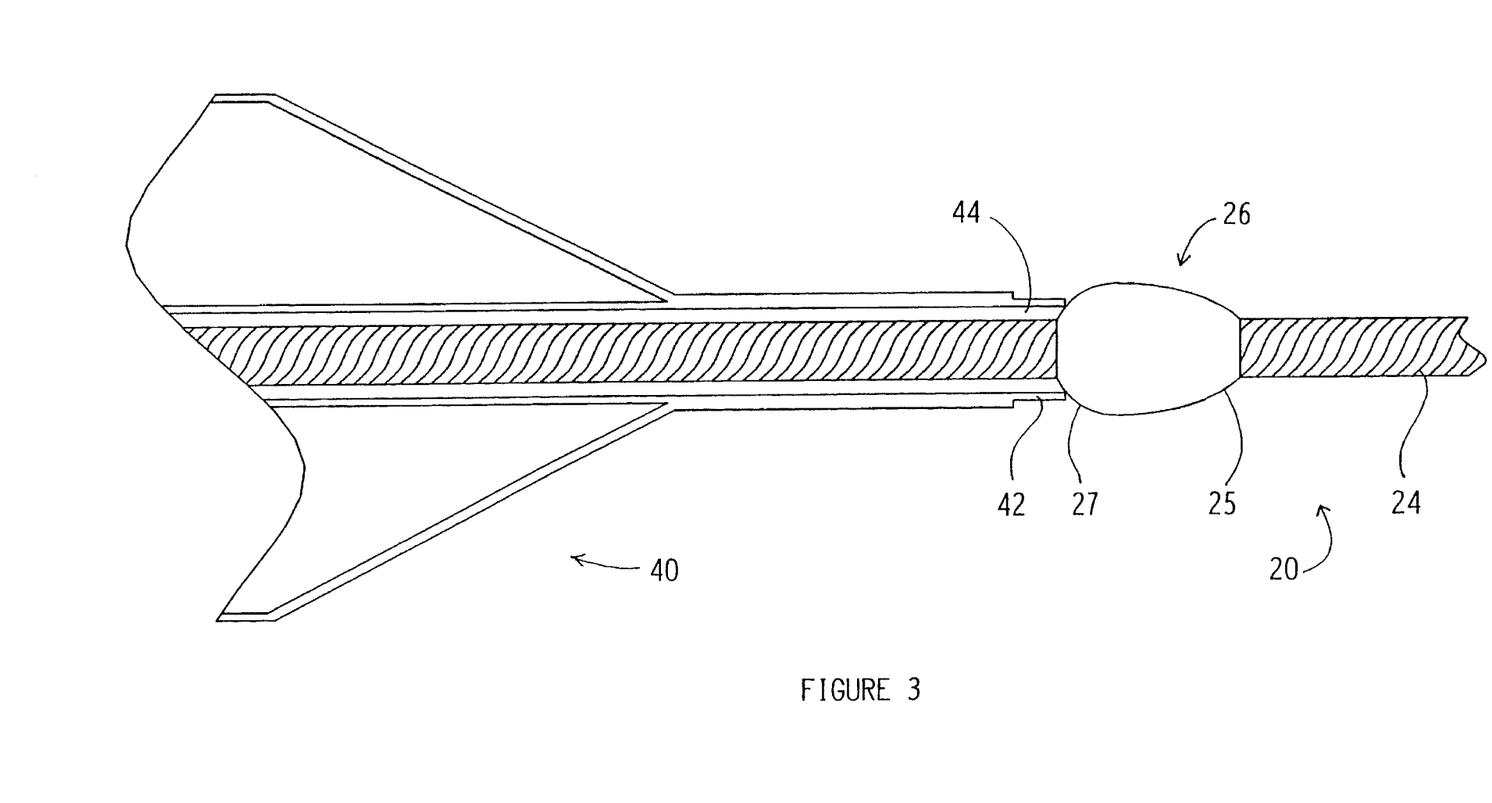
FIG. 3 shows a cutaway view the tip of a balloon catheter with the guide wire and tapered transition device in place.

FIG. 3 shows a close up view of the guide wire with tapered transition device 20 in place within a coronary dilatation catheter 40. The distal tip 42 of the dilatation catheter 40 is cut away to show the guide wire 20 within the distal lumen 44 of the catheter. The tapered transition device 26 is positioned just distal to the tip of the catheter 42. The diameter of the tapered transition device 26 closely matches the diameter of the catheter tip 42, and the smooth taper of the distal edge 25 of the tapered transition device 26 provides a smooth transition between the diameter of the guide wire coil 24 and the catheter tip. The taper on the proximal edge 27 of the tapered transition device 26, in this case, provides a centering mechanism to keep the guide wire 20 centered within the lumen 44 of the catheter.

Figure 4:
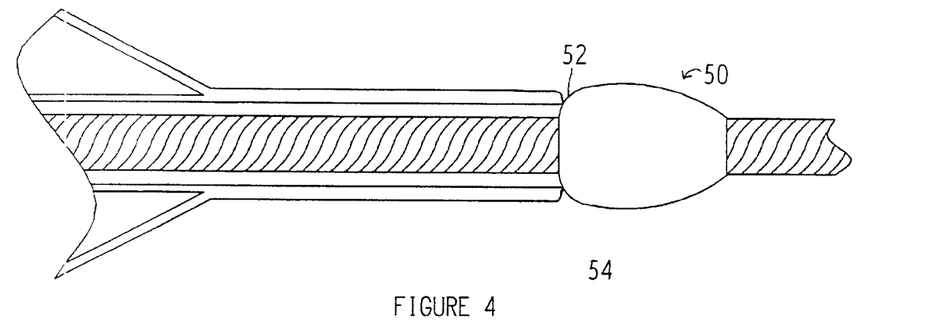
FIG. 4 shows an alternate embodiment of the tapered transition device.
Figure 5:
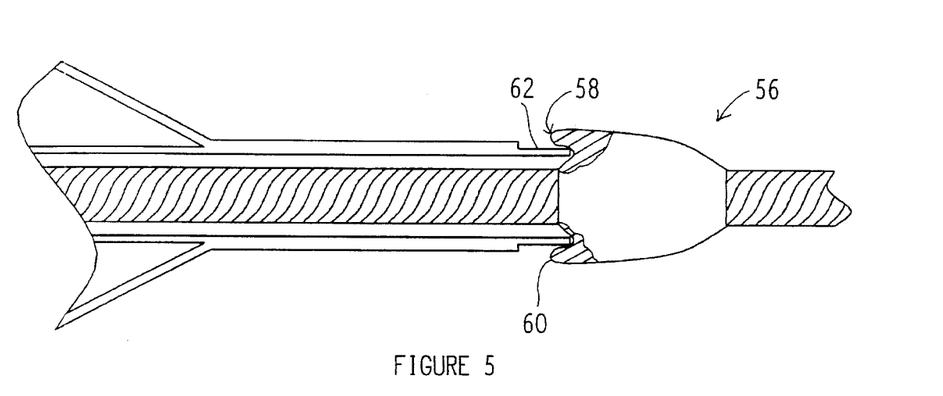
FIG. 5 shows an alternate embodiment of the tapered transition device.
Figure 6:
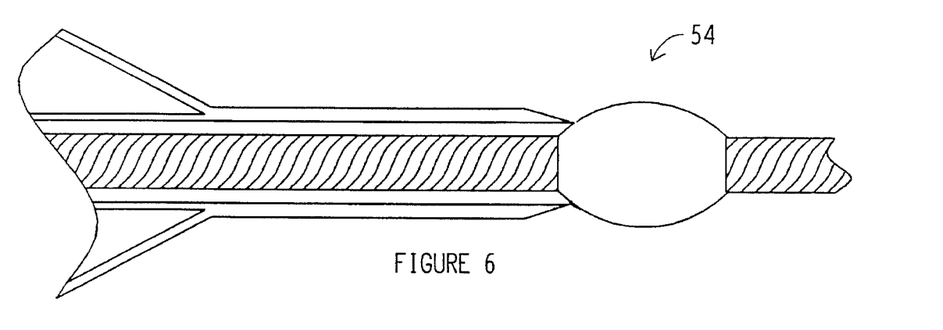
FIG. 6 shows an alternate embodiment of the tapered transition device.

Because there are significant variations in the distal tip geometry of coronary dilatation catheters currently on the market, FIGS. 4, 5 and 6 show alternative geometries for the tapered transition device to provide optimum performance with different catheters. FIG. 4 shows a variation of the tapered transition device 50 which has less of a taper on the proximal edge 52 of the device. The proximal edge 52 forms a shoulder which is rounded just enough so that it does not present any sharp edges. This geometry provides a closer match with catheters which are made with a relatively blunt distal end 54. FIG. 5 shows a variation of the tapered transition device 56 which has a proximal edge 58 designed with an outer lip 60 to surround and protect the distal tip 62 of the catheter. FIG. 6 shows a variation of the tapered transition device 54 which has symmetrical tapers on the proximal and distal edges.

Figure 7:
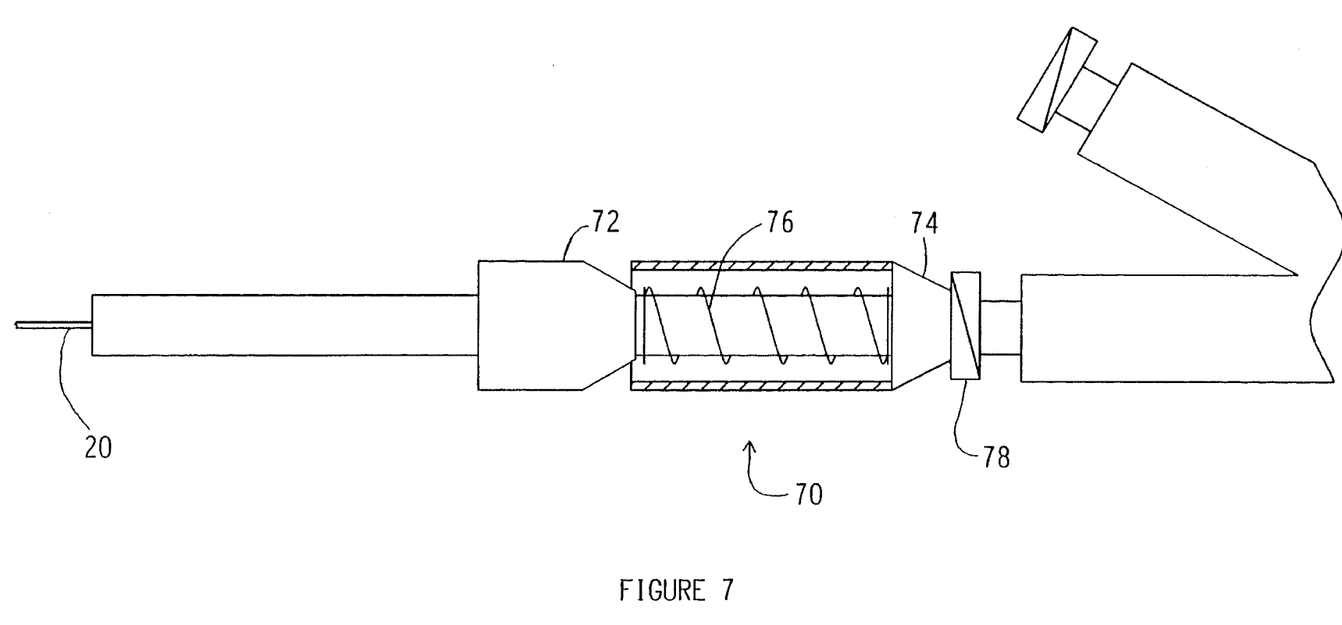
FIG. 7 shows the maneuvering handle for use with the guide wire.

FIG. 7 shows a cutaway view of a maneuvering handle 70 for use with the guide wire with tapered transition device 20. The maneuvering handle 70 provides a means for gripping the proximal end of the guide wire 20 and applying maneuvering forces for pushing, pulling and turning the guide wire 20. The maneuvering handle 70 has a gripping collet 72 which clamps onto the proximal end of the guide wire 20. In addition, the maneuvering handle 70 has a conical bearing surface 74 which nests into the luer fitting 78 on the proximal end of the dilatation catheter. The conical bearing surface 74 centers the maneuvering handle 70 and allows it to rotate with respect to the luer fitting 78. Between the gripping collet 72 and the conical bearing surface 74, there is a compression spring 76 which presses the conical bearing surface 74 against the luer fitting 78 to provide a light tension on the guide wire 20.

Figure 8:
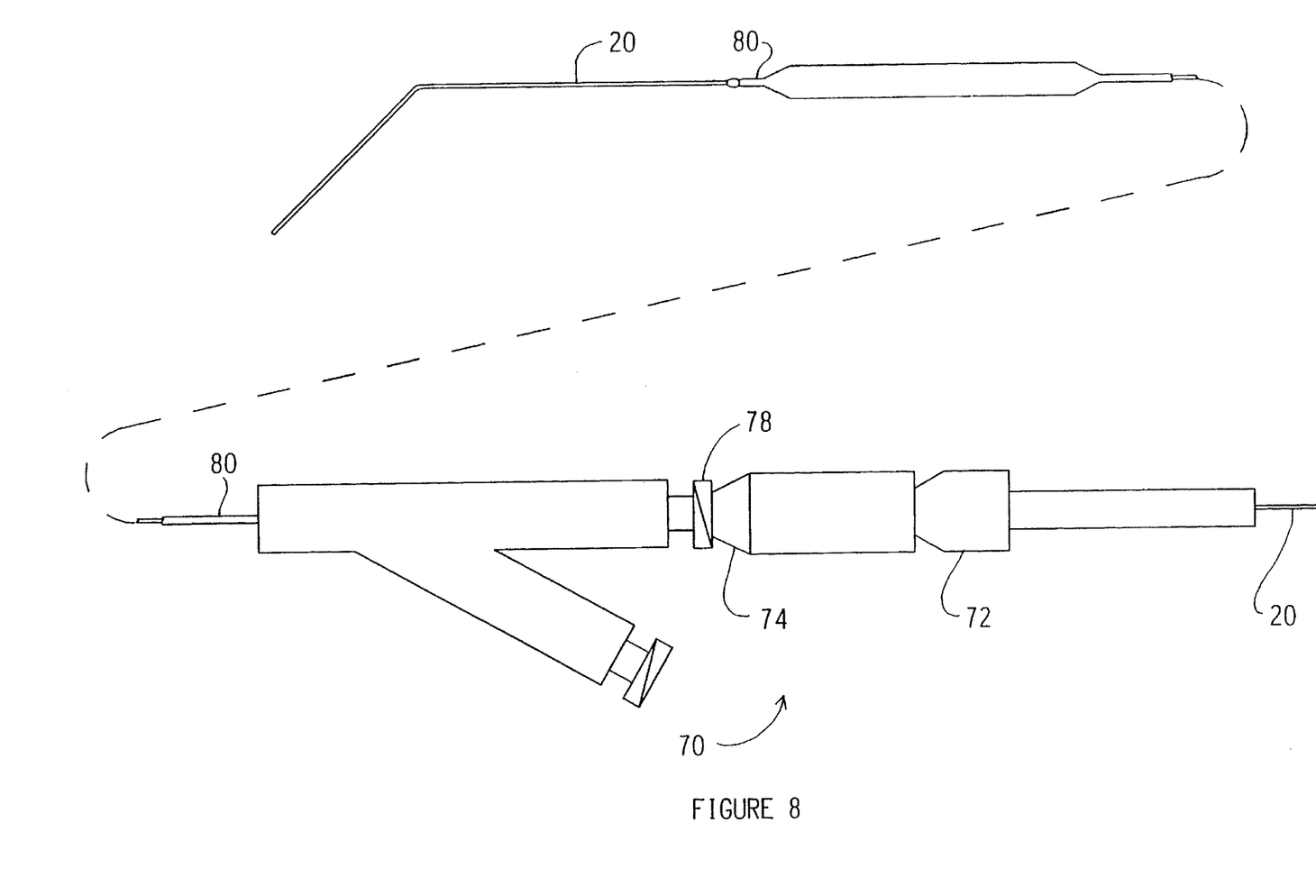
FIG. 8 shows an over-the-wire balloon dilatation catheter with the guide wire with tapered transition device and the maneuvering handle in place.

FIG. 8 shows an assembled dilatation catheter system using the guide wire with tapered transition device 20 and the maneuvering handle 70. The proximal end of the guide wire 20 is inserted into the distal lumen of the dilatation catheter 80 until the tapered transition device 20 is adjacent to the distal tip of the catheter 80. The maneuvering handle 70 is then placed over the proximal end of the guide wire 20 which is extending from the luer fitting 78 on the proximal end of the catheter 80. The conical bearing surface 74 is placed in contact with the luer fitting 78 and the compression spring 76 (not visible in this view) is compressed slightly before the gripping collet 72 is tightened onto the guide wire 20. The maneuvering handle 70 locks the catheter system together so that the guide wire 20 and the catheter 80 can be moved together as a single unit, while the guide wire 20 can still be rotated independently using the maneuvering handle 70.

Figure 12:
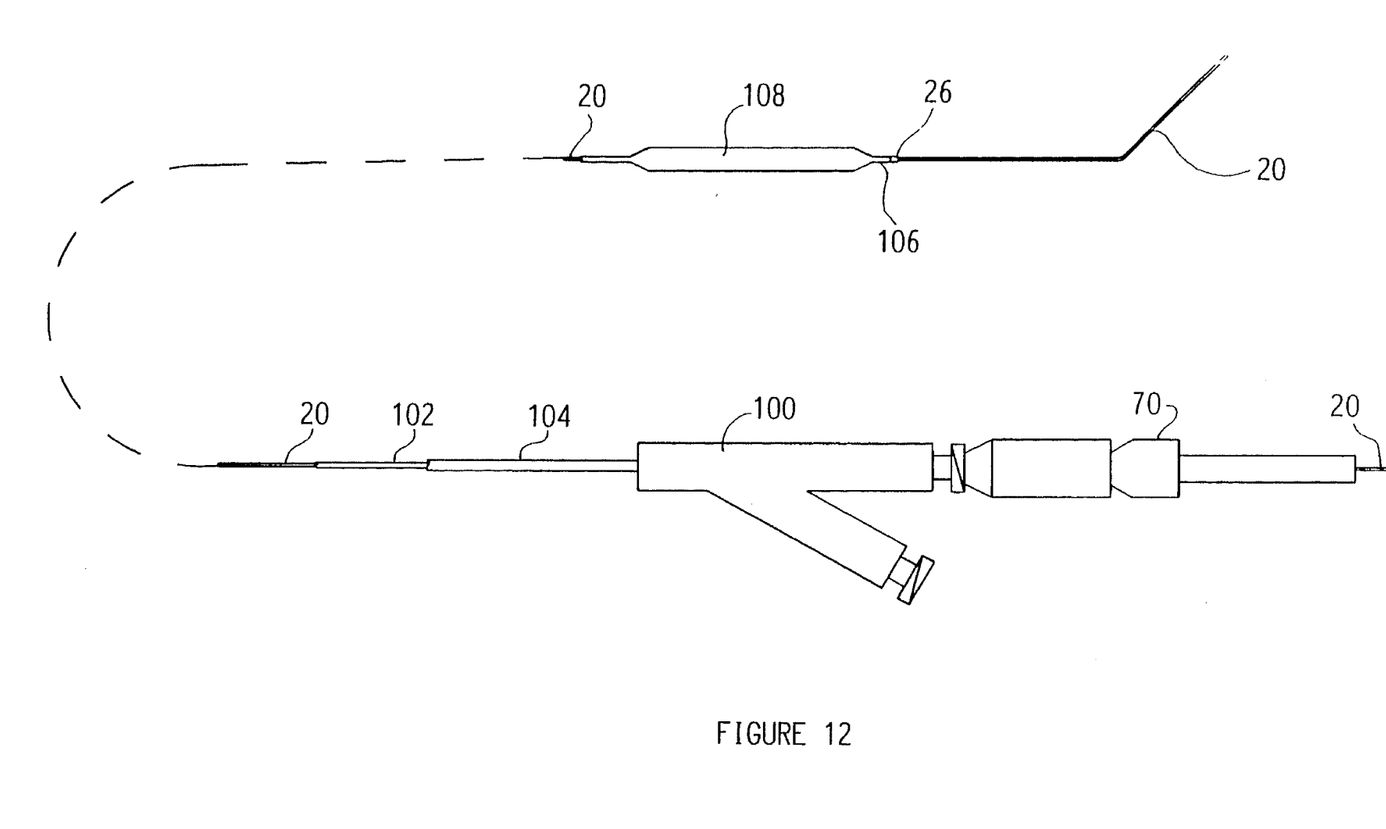
FIG. 12 shows an over-the-wire catheter with a reinforced proximal shaft for use with the improved guide wire.

FIG. 12 shows an improved version of a coronary angioplasty catheter 100 for use with the improved guide wire with tapered transition device 20. The proximal shaft 102 of the catheter 100 is externally reinforced with a relatively rigid tube 104. The tube 104 is preferably made from thin walled stainless steel hypodermic needle tubing, which is commonly know in the industry as "hypotubing." The thin walled tubing 104 reinforces the proximal end 102 of the catheter 100 to prevent bending. The length of the tubing 104 should be such that it is at least as long as the difference between the length of the coronary angioplasty catheter 100 and the coronary guiding catheter it is used with (not shown). This length is chosen so that when the coronary angioplasty catheter 100 is inserted into the guiding catheter, the tubing 104 will have entered the proximal end of the guiding catheter before the distal end of the catheter 106 with the dilatation balloon 108 attached exits from the distal end of the guiding catheter. When used with the maneuvering handle 70 previously described, the reinforced catheter 100 and the guide wire 20 can be manipulated as a unit by one hand on the maneuvering handle 70. The maneuvering handle 70 can be used to rotate the guide wire 20 and advance or retract the catheter 100 and guide wire 20 together. The reinforcing tubing 104 prevents the proximal end of the catheter 102 from buckling when it is pushed forward by the handle 70.

OPERATIONAL DESCRIPTION

In operation, the guide wire with tapered transition device 20 and the maneuvering handle 70 are assembled together with a dilatation catheter 80, as shown in FIG. 8. The assembled dilatation catheter system is inserted into a coronary guiding catheter and introduced into one of the coronary arteries using known methods. When the reinforced catheter 100 of FIG. 12 is used for this procedure, it simplifies the manipulation of the catheter and guide wire system, allowing the guide wire 20 to be rotated and the catheter 100 and guide wire 20 to be advanced or retracted as a unit by one hand on the maneuvering handle 70.

Figure 9:
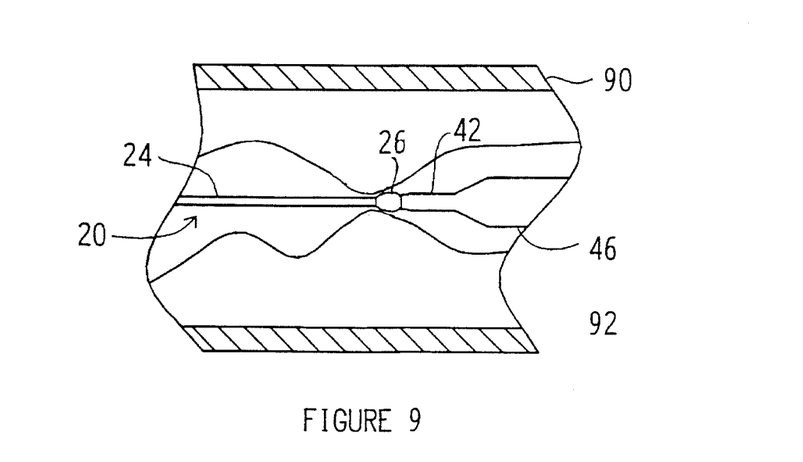
FIG. 9 shows an over-the-wire catheter using the guide wire with tapered transition device to pass a tightly stenotic lesion in an artery.

When the catheter system approaches a stenosis 92 in the coronary artery 90, as shown in FIG. 9, the distal coil spring 24 of the guide wire is the first part to cross the stenosis 92. Then, the tapered transition device 26 enters the stenosis 92. The tapered transition device 26 makes a smooth transition between the small diameter coil spring 24 and the larger diameter catheter tip 42. If the stenosis is very tight, the tapered transition device 26 will predilate the stenosis 92, making it easier to cross the stenosis with the deflated dilatation balloon 46. This predilation mechanism works effectively because the tapered transition device 26 is linked directly to the core wire of the guide wire, which can transmit greater pushing force to the site of the lesion. With a standard over-the-wire dilatation catheter system, the catheter body must transmit most of the necessary pushing force to get the catheter tip across the lesion. If the stenosis is particularly narrow, the catheter body will buckle and there will not be enough force transmitted to cross the lesion.

Figure 10:
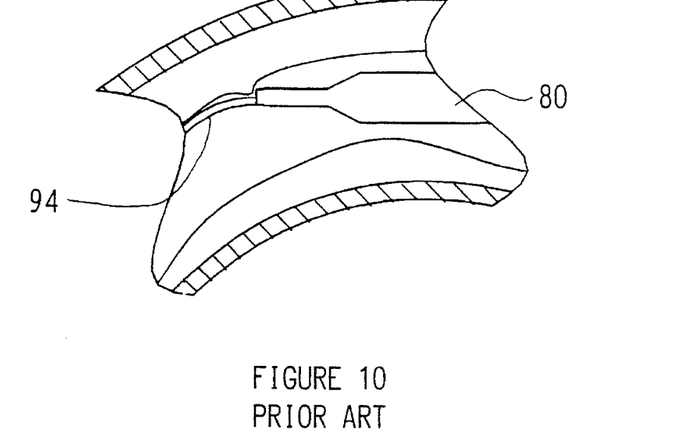
FIG. 10 shows an over-the-wire catheter using a prior art guide wire passing a turn in a tortuous artery.
Figure 11:
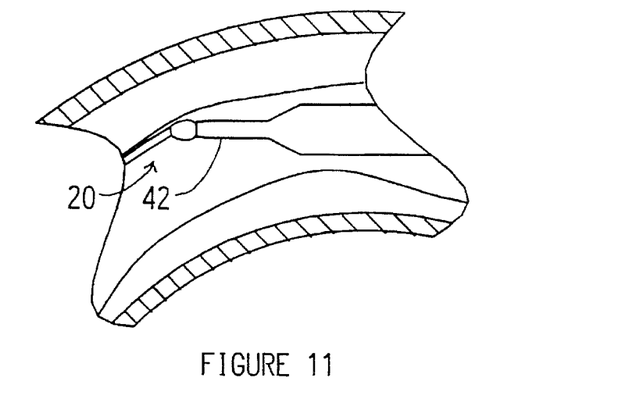
FIG. 11 shows an over-the-wire catheter using the guide wire with tapered transition device passing a turn in a tortuous artery.

The guide wire with tapered transition device 20 is also effective in helping the catheter system to maneuver through tortuous coronary arteries better than prior art guide wire devices. FIG. 10 shows an over-the-wire dilatation catheter 80 being advanced through a curve in a tortuous coronary artery using a prior art guide wire 94. Because there is an abrupt step between the small diameter guide wire and the larger diameter catheter tip, the catheter tip has a tendency to scrape the interior wall of the artery as it rounds the outside of a curve. This can damage the endothelial layer of the artery, potentially causing a dissection of the arterial wall or embolizing atherosclerotic material that may be dislodged from the arterial wall. As shown in FIG. 11, however, the guide wire with tapered transition device 20 centers the catheter tip 42 around the guide wire 20 and makes a smooth transition between the guide wire and the catheter tip for a smoother and less traumatic passage through the artery. There are no abrupt steps in the catheter system that would tend to scrape the arterial wall or dislodge any embolic material.

If it is desired to change dilatation catheters at any time during the procedure, this can easily be accomplished by removing the maneuvering handle, attaching a guide wire extension to the connector at the proximal end of the guide wire and performing a standard catheter exchange. Since the tapered transition device is distal to the catheter tip, it does not interfere in any way with the catheter exchange. Other variations of this operational description are of course possible. For example, the guide wire with tapered transition device can be used with rapid exchange PTCA catheters. The only change in the procedure necessary is that the spring in the maneuvering handle cannot bear against the proximal end of the rapid exchange catheter since the guide wire lumen does not extend the full length of the catheter. Rapid catheter exchanges can be accomplished as with a standard PTCA guide wire. The guide wire with tapered transition device can enhance the performance of a rapid exchange PTCA catheter because of its ability to predilate a tight stenosis and assist the catheter in crossing the lesion.

Although the examples given include many specificities, they are intended as illustrative of only some of the possible embodiments of the invention. Other embodiments and modifications will, no doubt, occur to those skilled in the art. For example, although the operational description above makes specific reference to PTCA catheters and procedures, the guide wire with tapered transition device can be used for many other diagnostic and therapeutic catheter procedures. For instance, the improved guide wire would also find application in procedures such as PTA, directional atherectomy, nondirectional atherectomy and laser angioplasty, to mention only a few of the many possibilities. Thus, the examples given should only be interpreted as illustrations of some of the preferred embodiments of the invention, and the full scope of the invention should be determined by the appended claims and their legal equivalents.

We claim:

1. In combination:

a catheter, said catheter having a proximal end and a distal end, said catheter having an internal lumen communicating with at least said distal end of said catheter, said internal lumen having an internal diameter, said distal end of said catheter having an external diameter, said internal lumen of said catheter extending substantially the full length of said catheter, a guide wire, said guide wire comprising an elongate guide wire body having a proximal end and a distal end, and a tapered transition device attached to said guide wire body intermediate said proximal and distal ends of said guide wire body, said guide wire body having a proximal external diameter proximal to said tapered transition device which is less than said internal diameter of said internal lumen, said guide wire body having a distal external diameter distal to said tapered transition device and said tapered transition device having a diameter which is greater than said distal external diameter of said guide wire body, said tapered transition device having a distal edge which is tapered to provide a smooth transition between said diameter of said tapered transition device and said distal external diameter of said guide wire body, and a maneuvering handle having a gripping means for gripping said guide wire body and a bearing means for rotatably bearing against said proximal end of said catheter and a spring means for exerting a force between said bearing means and said gripping means.

2. The combination of claim 1, wherein a portion of said guide wire body proximal to said tapered transition device is inserted into said internal lumen of said catheter and said tapered transition device is located distal to said distal end of said catheter.

3. The combination of claim 2, wherein said diameter of said tapered transition device is approximately equal to said external diameter of said distal end of said catheter and the tapered distal edge of said tapered transition device provides a smooth transition between said distal end of said catheter and said distal external diameter of said guide wire body.

4. The combination of claim 1, wherein said catheter further comprises an inflatable balloon portion which is inflatable to a diameter which is greater than said external diameter of said distal end of said catheter.

5. The combination of claim 1 wherein said catheter has a proximal portion and a distal portion, said proximal portion being relatively rigid with respect to said distal portion.

6. The combination of claim 5 wherein said proximal portion of said catheter is reinforced with a relatively rigid reinforcing member.

7. The combination of claim 5 wherein said proximal portion of said catheter is reinforced with a relatively rigid external tubing member.

8. A method of catheterization, comprising the steps of:

(a) providing a catheter, said catheter having a proximal end and a distal end, said catheter having an internal lumen communicating with at least said distal end of said catheter, said internal lumen having an internal diameter, said distal end of said catheter having an external diameter, said internal lumen of said catheter extending substantially the full length of said catheter, (b) providing a guide wire, said guide wire comprising an elongate guide wire body having a proximal end and a distal end, and a tapered transition device attached to said guide wire body intermediate said proximal and distal ends of said guide wire body, said guide wire body having a proximal external diameter proximal to said tapered transition device which is less than said internal diameter of said internal lumen, said guide wire body having a distal external diameter distal to said tapered transition device and said tapered transition device having a diameter which is greater than said distal external diameter of said guide wire body, said tapered transition device having a distal edge which is tapered to provide a smooth transition between said diameter of said tapered transition device and said distal external diameter of said guide wire body, (c) inserting said proximal end of said guide wire into said internal lumen at said distal end of said catheter until said tapered transition device is adjacent to said distal end of said catheter, (d) attaching a maneuvering handle to said proximal end of said guide wire, said maneuvering handle having a gripping means for gripping said guide wire body, and a bearing means for rotatably bearing against said proximal end of said catheter and a spring means for exerting a force between said bearing means and said gripping means, and (e) inserting said distal end of said guide wire and said distal end of said catheter into a passage in the body of a patient.

9. The method of claim 8, further comprising the step of:

(f) providing said catheter with an inflatable balloon portion which is inflatable to a diameter which is greater than said external diameter of said distal end of said catheter, maneuvering said inflatable balloon portion to a narrowing in said passage in the body of said patient and inflating said inflatable balloon portion.

10. In combination:

a catheter, said catheter having a proximal end and a distal end, said catheter having an internal lumen communicating with at least said distal end of said catheter, said internal lumen of said catheter extending substantially the full length of said catheter; said internal lumen having an internal diameter, said distal end of said catheter having an external diameter, a guide wire, said guide wire comprising an elongate guide wire body having a proximal end and a distal end, and a tapered transition device attached to said guide wire body intermediate said proximal and distal ends of said guide wire body, said guide wire body having a diameter which is less than said internal diameter of said internal lumen and said tapered transition device having a diameter which is greater than the diameter of said guide wire body, said tapered transition device having a distal edge which is tapered to provide a smooth transition between said diameter of said tapered transition device and said diameter of said guide wire body, and a maneuvering handle having a gripping means for gripping said guide wire body, and a bearing means for rotatably bearing against said proximal end of said catheter and a spring means for exerting a force between said bearing means and said gripping means.

11. The guide wire of claim 10, wherein said diameter of said tapered transition device is at least 0.005 inches greater than said distal external diameter of said guide wire body.

12. The guide wire of claim 10, wherein said diameter of said tapered transition device is at least 0.010 inches greater than said distal external diameter of said guide wire body.

13. The combination of claim 10, wherein a portion of said guide wire body proximal to said tapered transition device is inserted into said internal lumen of said catheter and said tapered transition device is located distal to said distal end of said catheter.

14. The combination of claim 13, wherein said diameter of said tapered transition device is approximately equal to said external diameter of said distal end of said catheter and the tapered distal edge of said tapered transition device provides a smooth transition between said distal end of said catheter and said diameter of said guide wire body.

15. The combination of claim 10, wherein said catheter further comprises an inflatable balloon portion which is inflatable to a diameter which is greater than said external diameter of said distal end of said catheter.

16. The combination of claim 10 wherein said catheter has a proximal portion and a distal portion, said proximal portion being relatively rigid with respect to said distal portion.

17. The combination of claim 16 wherein said proximal portion of said catheter is reinforced with relatively rigid reinforcing member.

18. The combination of claim 17 wherein said proximal portion of said catheter is reinforced with a relatively rigid external tubing member.

19. The combination of claim 10, wherein said guide wire body comprises a core wire which extends substantially the length of said guide wire, said core wire having a tapered distal section extending to form said relatively flexible distal portion.

20. The combination of claim 19, wherein said relatively flexible distal portion of said guide wire body further comprises a flexible coil spring which surrounds said tapered distal section of said core wire.

\* \* \* \* \*